(12) United States Patent
Hiraide et al.

(10) Patent No.: US 6,232,345 B1
(45) Date of Patent: May 15, 2001

(54) CEREBRAL FUNCTION IMPROVING AGENTS

(75) Inventors: Atsushi Hiraide, Toyonaka; Sekiko Dohi, Shimizu; Motohisa Suzuki, Shimizu; Yoshihiro Shiba, Shimizu, all of (JP)

(73) Assignee: Shimizu Pharmaceutical Co., Ltd., Shizouka Shimizu (JP)

( * ) Notice: Subject to any disclaimer, the term of this patent is extended or adjusted under 35 U.S.C. 154(b) by 0 days.

(21) Appl. No.: 09/527,241

(22) Filed: Mar. 17, 2000

Related U.S. Application Data (63) Continuation of application No. 08/756,747, filed on Jan. 26, 1996, now Pat. No. 6,136,862.

(30) Foreign Application Priority Data

| Dec. 1, 1995 | (JP) | 7-337750 |
| Jul. 31, 1996 | (JP) | 8-202671 |
| Aug. 1, 1996 | (JP) | 8-202676 |
| Oct. 24, 1996 | (JP) | 8-299247 |

(51) Int. Cl.$^7$ ................................. A61K 31/22
(52) U.S. Cl. ................................. 514/546
(58) Field of Search ................... 514/578, 546

(56) References Cited

U.S. PATENT DOCUMENTS

| 4,346,107 | 8/1982 | Cavazza et al. . |
| 5,116,868 | 5/1992 | Chen et al. . |

FOREIGN PATENT DOCUMENTS

| 2 126 082 | 11/1983 | (GB) . |
| 58-201746 | 11/1983 | (JP) . |

OTHER PUBLICATIONS

Chang et al., Can J. Physiol. Pharmacol., "Hypoxia and beta–hydroxybutyrate acutely, reduce glucose. extraction by the brain in anesthetized dogs", vol. 71, No. 7, 1993, pp 465–472.

Robertson et al., Stroke Dietary non–protein calories and cerebral infarction size in rats, vol. 23, No. 4 pp 1993 564–568.

Artru et al., J. of Neurochemistry, "gamma–hydroxybutyrate: cerebral metabolic, vasclar, and protective. effects", vol. 35, No. 5, 1980, pp 1114–1119.

Bendikov et al., Biull. Eksp biol. Med., "Effect of sodium hydroxybutyrate on cerebral circulation and reginal vasomotor reflexes", vol. 88, No. 11, 1979, pp 555–557.

Atarskaya et al., Kirg. Med. Inst., "Anti–oedematous agent for cerebral cedema experiments—comprises cobalt homo–pantothenato–ascorbinate, administered by intraperitoneal injection", 02/94.

Denki Kagaku Kogyo KK, "Gamma amino beta hydroxybutyric acid preparation hydrolysis hydroxy pyrrolidon cerebral function metabolism adjust", 09/92.

Gueld et al., Chemical abstracts for 1991; 95112.

Owen et al., "Brain Metabolism During Fasting", The Journal of Clinical Investigation, vol. 46, No. 10,. (1967), pp 1585–1595.

Fuji et al., Study on Administration of Ketone After Acute Cerebran Injury:, Jpn J. Acute Med., vol. 4, No. 5, 1993, pp 484.

Go et al., "Protective Effect of Fasting Upon Cerebral Hypoxic–Ischemic Injury", Metabolic Brain Disease, vol. 3, No. 4, 1988, pp 257–263.

Gueldry et al., "Effect of 1,3–Butaneodiol on Cerebral Energy Metabioliism, Comparison With B–Hydroxybutryate", Metabolic Brain Disease, vol. 9, No. 2, 1994, pp 171–181.

Rising et al., "Hypoxia–Induced Increases in Hyploxic Tolerance Augmented by b–Hydroxybutyrate in Mice", Stroke, vol. 20, No. 9, 1988, pp 1219–1225.

Chang et al., "Hypoxia and B–Hydroxybutrate Acutely Reduce Glucose Extraction by the brain in Antheshetized Dogs", Can J. Physiol. Pharmacol., vol. 71, 1993, pp 465–472.

Marie et al., "Protective Action of 1, 3–Butanediol in Cerebral Ischemia, A Neurologic, Histologic, and. Metabolic Study", Journal of Cerebral Blood Flow and Metabolism, vol. 7, 1987, pp 794–800.

Kirsch et al., "Hypoxia Induced Preferential Ketone Utilization by Rat Brain Slices", Stroke, vol. 15, No. 2 1994), pp 319–323.

Kirsch et al., "Role of Tissue Lactate and Substrate Availability in 1, 3–Butanediol–Enhanced Hypoxic. Survival in the Mouse", Stroke, vol. 14, No. 6, 1983, pp 971–978.

Roeder et al., "Competition Among Oxidizable Substrates in Brains of Young and Adult Rats", Biochem. J.,. vol. 219 1984, pp 125–130.

Seccombe et al., "Fetal Utilization of Maternally Derived Ketone Bodies for Lipogenesis in the Rate",. Biochemica et Biophysica Acta, vol. 488, 1977, pp 402–416.

*Primary Examiner*—James H. Reamer
(74) *Attorney, Agent, or Firm*—Foley & Lardner (57) ABSTRACT

A cerebral function improving agent containing as the active ingredient a compound represented by the following formula:

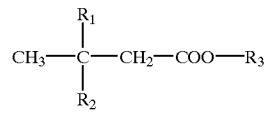

wherein $R_2$ represents a hydrogen atom when $R_1$ is a hydroxyl group;

or $R_1$ and $R_2$ in combination represent an oxo group;

$R_3$ represents a hydrogen atom, an alkali metal, or a monohydric, dihydric or trihydric alcohol residue;

which may be an oligomer composed of 2–10 molecules when $R_1$ represents a hydroxyl group and $R_2$ and $R_3$ represent hydrogen atoms.

The agent supresses cerebral edema, protects cerebral function, activates cerebral metabolisms and reduces the extent of cerebral infarction.

8 Claims, 6 Drawing Sheets

CEREBRAL FUNCTION IMPROVING AGENTS

This application is a continuation application of U.S. Ser. No. 08/756,747, filed Nov. 26, 1996 now U.S. Pat. No. 6,136,862.

BACKGROUND OF THE INVENTION

1. Field of the Invention

The present invention relates to cerebral function improving agents, more specifically, those agents which act by suppressing cerebral edema, protecting cerebral function, activating cerebral metabolism, or reducing the extent of cerebral infarction.

2. Description of the Prior Art

In recent years, an increasing number of individuals have suffered from cerebrovascular diseases or cerebral injury due to traffic accidents, etc. These conditions are often associated with cerebral edema and impairment of cerebral metabolism. This trend is probably due to dietary changes that have increased fat intake as well as the increased prevalence of cerebrovascular diseases along with the increase in the elderly population.

Cerebral edema, which impairs cerebral function, is defined as an increase in the water content of the brain parenchyma which results in an increase in cerebral volume. Cerebral edema not only causes transient metabolic and functional impairment of neurons but also increases the intracranial pressure, leading to impairment of the cerebral circulation and metabolism. These changes further aggravate cerebral edema, which may progress to brain herniation with an occasional fatal outcome.

Cerebral edema can be classified into two etiologic types, which are vasogenic edema and cytotoxic edema.

1. Vasogenic edema: Vasogenic edema occurs due to the interstitial retention of serum components leaking from vessels into the cerebral tissue as a result of dysfunction of the blood-brain barrier of the cerebral capillaries. Edema of this type is typically associated with cerebral contusion, tumor, abscess, or hemorrhage, and intracranial hematoma.

2. Cytotoxic edema: Cytotoxic edema results from cell membrane injury caused by lactate accumulation when energy metabolism is impaired in the cerebral parenchyma. Edema of this type is typically associated with cerebral ischemia, hypoxemia, and lactic acidosis.

The current therapeutic approaches to these conditions include:

(1) Intravenous hypertonic fluids: Hypertonic fluids relieve cerebral edema by increasing the blood osmotic pressure and thus attracting the interstitial fluid back into the vessels. However, a rebound phenomenon is observed after discontinuation of the hypertonic infusion because the blood osmotic pressure decreases again.

(2) Corticosteroids: Corticosteroids are used in the treatment of vasogenic edema associated with cerebral tumor or abscess because they promote the function of the blood-brain barrier, stabilize cell membranes, and suppress inflammatory responses and the production of cerebrospinal fluid. However, it has been reported that corticosteroids aggravate ischemic neuronal damage.

(3) Antioxidants: Antioxidants relieve cerebral edema by scavenging free radicals generated due to ischemia or cellular injury.

(4) Ca-channel blockers: Ca-channel blockers are expected to inhibit delayed neuronal death that results from calcium influx into cerebral neurons in the presence of edema. However, Ca-channel blockers have a vasodilatory effect, and thus may aggravate cerebral edema by increasing local blood flow.

(5) Barbiturates: Barbiturates protect the brain against ischemia because they reduce cerebral metabolic activity (cerebral oxygen and glucose consumption) and thus inhibit further lactate accumulation and acidosis. However, barbiturates exert these beneficial effects at doses which also cause respiratory depression and cardiovascular toxicity. Therefore, careful respiratory and circulatory management is required during their use.

Thus, there have been demands for development of drugs which are effective for the prevention and treatment of cerebral edema and have no potential for inducing a rebound response or other toxicities.

The present inventors have found that β-hydroxybutyric acid, its salts, and its esters, which had not previously been evaluated for their effect on cerebral function, suppressed cerebral edema by activating cerebral metabolism. These compounds were also found to protect the brain mitochondria by activating cerebral metabolism and thus to reduce the extent of cerebral infarction caused by ischemia.

Therefore, the present invention provides cerebral function improving agents which specifically act by suppressing cerebral edema, protecting cerebral function, activating cerebral metabolism, or reducing the extent of cerebral infarction.

SUMMARY OF THE INVENTION

The present invention provides cerebral function improving agents containing as the active ingredient the compounds represented by the following formula (1):

(1)

wherein $R_2$ represents a hydrogen atom when $R_1$ is a hydroxyl group;

or $R_1$ and $R_2$ are combined together to form an oxo group;

$R_3$ represents a hydrogen atom, an alkali metal, or a monohydric, dihydric or trihydric alcohol residue.

The compound may be an oligomer composed of 2–10 molecules when $R_1$ represents a hydroxyl group and $R_2$ and $R_3$ represent hydrogen atoms.

In other words, an object of the present invention is to provide cerebral function improving agents containing the compounds of formula (1), and more specifically, to provide cerebral function improving agents containing β-hydroxybutyric acid, sodium β-hydroxybutyrate, and/or esters of β-hydroxybutyric acid.

The compounds of formula (1), the active ingredient of the cerebral function improving agents according to the present invention, act by suppressing cerebral edema, protecting cerebral function, activating cerebral metabolism, or reducing the extent of cerebral infarction.

Accordingly, another object of the present invention is to provide cerebral edema suppressing agents, cerebral function protecting agents, cerebral metabolic activators, and cerebral infarction reducing agents containing the compounds of formula (1) as the active ingredient

BRIEF DESCRIPTION OF THE DRAWINGS

The figures show the results of the animal studies described later in the present specification.

DETAILED DESCRIPTION OF THE INVENTION

β-hydroxybutyric acid, a representative type of the compounds of formula (1), is a ketone (like acetone and acetoacetic acid) produced by degradation of fatty acids in the liver. Since β-hydroxybutyric acid is detected in the urine of diabetic patients and since the blood level of the compound increases during starvation, it had been thought to be the end product of metabolism and unnecessary for the living body until Owen et al. reported the results of a metabolic study in obese patients [J. Clin. Invest. 46(10), 1589–1595 (1967)]. Their results indicated that β-hydroxybutyric acid was utilized as an energy source instead of glucose in the brains of obese patients fasted for 5–6 weeks.

β-hydroxybutyric acid is a water-soluble, low molecular weight compound (M.W. 104). One gram of β-hydroxybutyric acid has 3.8 kcal of energy. During normal metabolism, the blood level of β-hydroxybutyric acid is only 0–3 mg/dl and the compound is excreted in the urine and expired air without being utilized. During fasting or starvation, however, the blood level rises to 20–30 mg/dl or higher and utilization commences. β-hydroxybutyric acid can be substituted for glucose as an energy source during fasting and starvation. It is metabolized and utilized by vital organs and tissues excluding the liver (i.e., the heart, kidneys, brain, and muscles).

Japanese Patent Kokai No. 201746/'83 discloses that salts of 3-hydroxybutyric acid and compositions containing the same protect myocardial metabolism. In addition, Fujii et al. [Jpn. J. Acute Med., 4(5), 484 (1993)] reported that intravenous administration of β-hydroxybutyric acid increased the ketone level and decreased the lactate level in the cerebrospinal fluid after acute cerebral injury.

The compounds of formula (1), however, have not been reported to improve cerebral function by improving impaired cerebral metabolism, suppressing cerebral edema, protecting cerebral function, or reducing the extent of cerebral infarction.

The present inventors have found that intravenous pretreatment with β-hydroxybutyric acid prolonged the survival time of animals given a lethal intravenous dose of potassium cyanide (KCN).

KCN is believed to show cytotoxicity by reducing the oxygen supply to the electron transport system and blocking ATP production through the inhibition of mitochondrial cytochrome oxidase. It has been reported that these effects of KCN can only be antagonized by promotion of cerebral glucose uptake, activation of the mitochondrial succinate oxidase system, and an increase in cerebral blood flow. The present inventors observed that KCN-induced death was delayed by continuous intravenous infusion of β-hydroxybutyric acid. β-hydroxybutyric acid, the blood level of which probably increased during continuous infusion, may have exerted this effect by promoting cerebral ATP production and accumulation. That is, continuous infusion of β-hydroxybutyric acid probably prolonged survival by enhancing the tolerance of cerebral mitochondria to anoxia subsequently induced by a lethal dose of KCN.

The present inventors have also found that simultaneous intravenous administration of β-hydroxybutyric acid prevented the development of cerebral edema in animals with cerebral ischemia caused by ligation of the bilateral common carotid arteries. In that study, high cerebral ATP levels were maintained in animals treated with β-hydroxybutyric acid. Based on this finding, β-hydroxybutyric acid may have suppressed cerebral edema by the following mechanisms: it may be metabolized and enter the TCA cycle to promote ATP production or suppress ATP consumption. This may have maintained a high activity of $Na^+/K^+$-ATPase, which could then actively pump retained sodium and water out of the cells.

Furthermore, the present inventors have found that administration of β-hydroxybutyric add during ligation of the middle cerebral artery and subsequent reperfusion markedly reduced the extent of cerebral infarction due to acute ischemia induced by arterial ligation. β-hydroxybutyric acid may have exerted this effect by improving cerebral metabolism and protecting the brain mitochondria against ischemia.

The present invention provides cerebral function improving agents containing as the active ingredient the compounds of formula (1), wherein $R_2$ represents a hydrogen atom when $R_1$ is a hydroxyl group; or $R_1$ and $R_2$ are combined together to form an oxo group; $R_3$ represents a hydrogen atom, an alkali metal such as sodium, potassium and lithium, or a monohydric, dihydric or trihydrc alcohol residue. Examples of the alcohol residue include $C_1$–$C_{12}$ monohydric alcohols such as methanol, ethanol and butanol, dihydric alcohols such as ethylene glycol, 1,3-butanediol and 2-butene-1,4diol, trihydric alcohols such as glycerin, and acids such as tartaric acid and succinic acid. The compound may be an oligomer composed of 2–10 molecules when $R_1$ represents a hydroxyl group and $R_2$ and $R_3$ represent hydrogen atoms.

Examples of the compounds of formula (1) include acetoacetic acid, β-hydroxybutyric acid, sodium β-hydroxybutyrate, and esters of β-hydroxybutyric acid. The esters may include those containing methanol, ethanol, and glycerin (mono-, di- and tri-esters).

The cerebral function improving agents of the present invention may be indicated for the treatment of vasogenic edema associated with cerebral injury, tumor, or hemorrhage, intracranial hematoma or late cerebral ischemia, and cytotoxic edema due to cerebral ischemia, severe brain injury, or hypoxemia.

The cerebral function improving agents of the present invention are preferably administered by intravenous infusion at a constant rate in parenteral fluid, but can also be administered via enteral alimentation or via intravenous injection. These agents are desirably used in the form of an aqueous solution.

In general, these agents may be added to parenteral fluid at a concentration of 5–500 mM, and administered at a rate of 1–2 ml/kg/hr although the optimum concentration depends on the patient's weight The concentration range of these agents in parenteral fluid may be preferably 10–300 mM, but more preferably 20–100 mM.

In general, these agents may preferably be administered for 1–7 days, although the duration of administration also depends on the patient's initial condition and response.

The cerebral function improving effects of the compounds of formula (1) are illustrated below by way of Examples.

A): Cerebral edema suppressing effect:

Example 1

Relationship between the dose and the effect of sodium β-hydroxybutyrate

The suppressive effect of sodium β-hydroxybutyrate on cerebral edema induced by ligation and severing of the bilateral common carotid arteries was studied in male Wistar rats (weighing 158.8 ±1.2 g). Solutions of sodium β-hydroxybutyrate were prepared at concentrations of 2.5, 5.0, 10, 20, 40, 80, 160, and 320 mM and administered at a rate of 10 ml/kg/hr for 5 hours. Accordingly, the doses of sodium β-hydroxybutyrate administered were 3.1, 6.3, 12.5, 25, 50, 100, 200 and 400 mg/kg/hr, respectively.

Rats were operated on under anesthesia which was introduced with ether and maintained by inhalation of a mixture of isoflurane/nitrous oxide/oxygen (0.5:70:30). A midline incision was made in the neck and the connective tissue was carefully dissected to avoid injury to the vagus nerve while exposing the bilateral common carotid arteries.

For test drug administration, the right external jugular vein was cannulated and the other end of the cannula was led out through the back of the animal. Then the common carotid artery was ligated at two points (head side and heart side) and severed between the two ligatures. The skin incision was sutured and each rat was immediately given physiological saline or one of the sodium β-hydroxybutyrate solutions by continuous intravenous infusion using an infusion pump (10 ml/kg/hr for 5 hours).

In sham-operated rats, the bilateral common carotid arteries were exposed in the same way and the skin incision was closed without arterial ligation and severing.

On completion of administration, each rat was decapitated, and the whole brain was isolated immediately. After removal of the cerebellum and the medulla oblongata, the wet weight of the cerebrum was measured. The cerebrum was then dried at 105° C. for 24 hours, after which the dry weight was measured. The cerebral water content was calculated by using the following formula:

Cerebral water content (%)=(wet weight of the cerebrum−dry weight of the cerebrum)/wet weight of the cerebrum×100.

Figure 1:
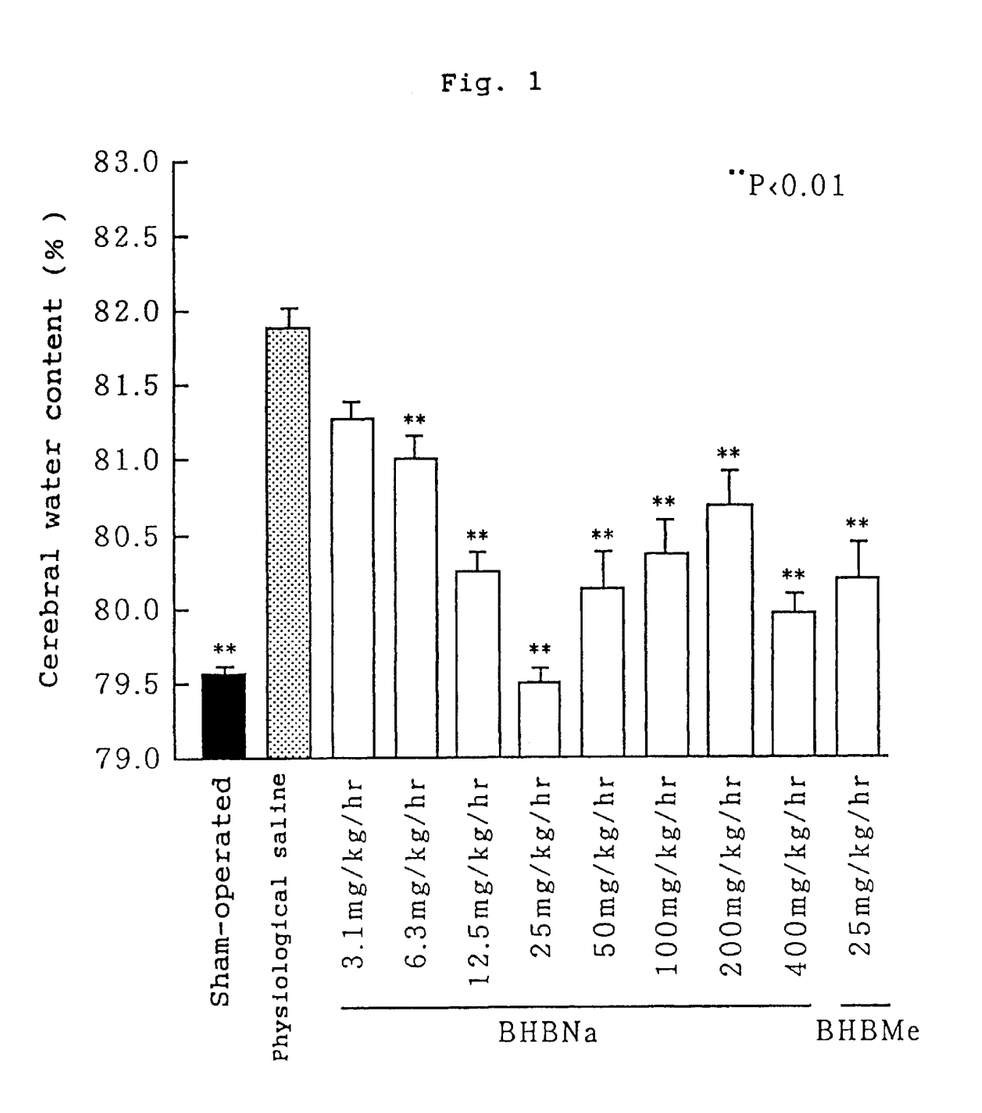
FIG. 1 shows the relationship between the dose of sodium β-hydroxy-butyrate or methyl β-hydroxybutyrate and the cerebral water content.

As shown in FIG. 1, the cerebral water content was related to the dose of sodium β-hydroxybutyrate.

(In FIG. 1, BHBNa represents sodium β-hydroxybutyrate, while BHBMe represents methyl β-hydroxybutyrate.)

The cerebral water content was 79.56±0.05% in sham-operated rats. In rats receiving physiological saline following ligation of the bilateral common carotid arteries, the cerebral water content was significantly higher than in the sham-operated group, indicating the onset of cerebral edema.

In all groups treated with sodium β-hydroxybutyrate, the cerebral water content was lower than in the physiological saline group and the difference was statistically significant ($p<0.01$) at doses of 5 mM or more. These results indicate that sodium β-hydroxybutyrate is effective for the prevention and treatment of cerebral edema.

Example 2

Relationship between the dose and the effect of methyl β-hydroxybutyrate

By using the same procedures described above, methyl β-hydroxy-butyrate was administered to rats at a dose of 25 mg/kg/hr for 5 hours. The results are also shown in FIG. 1.

Example 3

The following components in the specified amounts were used to prepare a parenteral solution according to the appropriate procedures:

Methyl β-hydroxybutyrate 2.42 g
Sodium chloride 2.05 g
Potassium chloride 1.47 g
Glucose 50.00 g These components were dissolved in about 950 ml of water, and the pH was adjusted to 7.0 with sodium hydroxide. Then, water was added to the solution to make it exactly 1,000 ml. The solution thus prepared was filtrated through a 0.45 μm pore filter. The filtrate was filled in a 500 ml glass vial and autoclaved to give a precipitate-free, colorless parenteral solution.

Using this solution, the effect of methyl β-hydroxybutyrate on cerebral edema was assessed in the same animal model as mentioned above in Example 1. In all rats treated with this solution, the cerebral water content was lower than in the physiological saline-treated group, indicating that methyl β-hydroxy-butyrate suppressed the development of cerebral edema.

B): Cerebral function protecting effect:

Example 4

(Materials and methods)
1. Test animals

Male Wistar rats aged 6–9 weeks (Japan S.L.C. Ltd.) were used. The animals were maintained at 23±3° C. and 55±15% humidity with lights on for 12 hours daily (from 7:00 to 19:00). They were fed a pellet diet (MF, Oriental Yeast Co., Ltd.) and tap water ad libitum. The number of the animals per group was 6–8.
2. Test and control drugs
   1) Test drug
      Sodium β-hydroxybutyrate (purity 99.8%)
   Samples of the lot used in the study showed no changes in quality when tested after completion of the study. It was confirmed that the prepared solutions were stable for at least 1 week and that they were prepared at proper concentrations.
   2) Control drug
      (1) Physiological saline JP
         Manufacturer: Plant of Otsuka Pharumaceutical Co., Ltd.
      (2) Grenol (brand name)
         Composition (content per 100 ml)
            Concentrated glycerin 10 g
            Fructose 5 g
            Sodium chloride 0.9 g
         Manufacturer: Shimizu Pharnaceutical Co., Ltd.
3. Administration The doses of sodium β-hydroxybutyrate tested were 50 and 100 mg/kg/hr (The solutions were prepared at 80 mM and 160 mM, respectively.), while Grenol was given at the recommended dinical dose (5 ml/kg/hr). In all groups, the solutions were administered at a rate of 5 ml/kg/hr for 1 hour via a cannula in the right external jugular vein. Another group received sodium β-hydroxybutyrate at a dose of 100 mg/kg/hr for 3 hours to study the influence of the administration period on the effect of the test drug.

4. Procedures

Rats were operated on under anesthesia which was introduced with ether and maintained by inhalation of a mixture of isoflurane/nitrous oxide/oxygen (0.5:70:30). The right external jugular vein was cannulated, and the other end of the cannula was fixed to the muscles of the back. Via the cannula, the specified dose of the test or control drug was administered followed immediately by potassium cyanide (KCN: 3 mg/kg). The survival time was defined as the interval from the administration of potassium cyanide to the onset of respiratory arrest.

5. Statistical analysis

Data are expressed as the mean ± standard error (S.E.). Differences between the groups were tested for significance by using one-way ANOVA. When a significant difference was detected between the groups, Dunnett's multiple comparison test was performed. The level of significance was set at $p<0.05$.

(Results)

Figure 2:
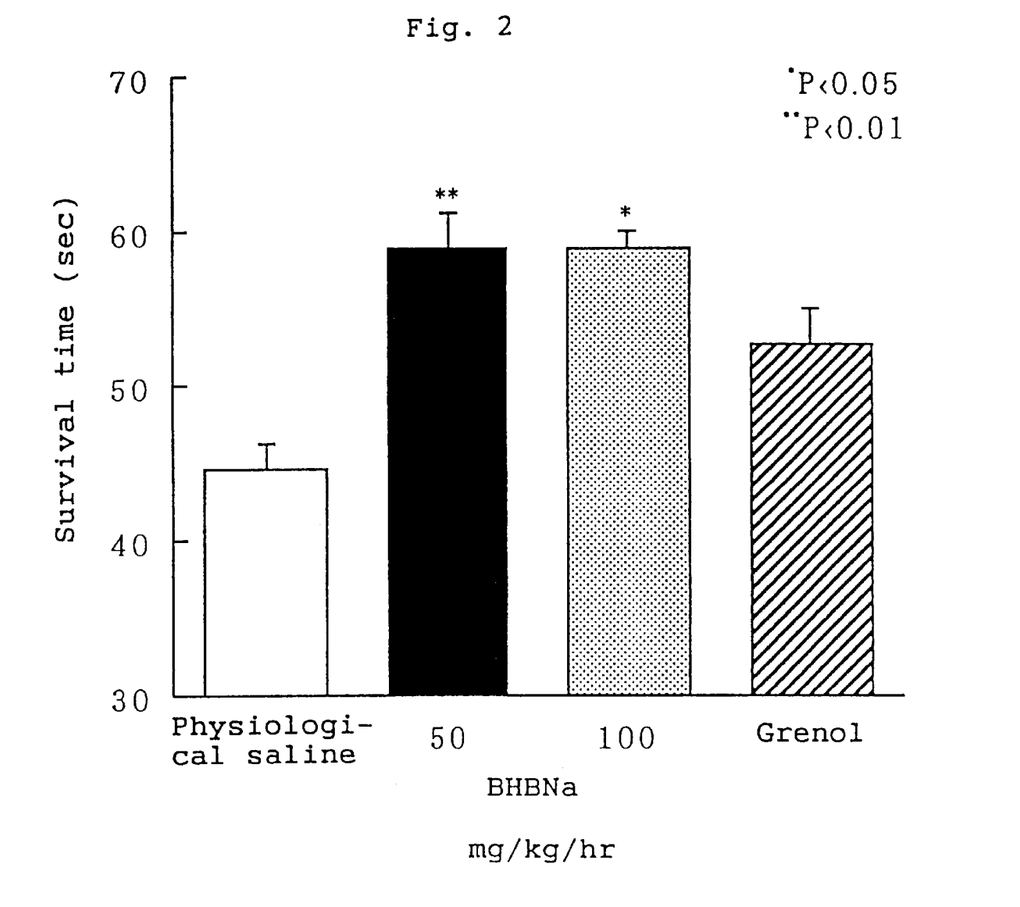
FIG. 2 shows the relationship between the dose of sodium β-hydroxy-butyrate and the survival time.
Figure 3:
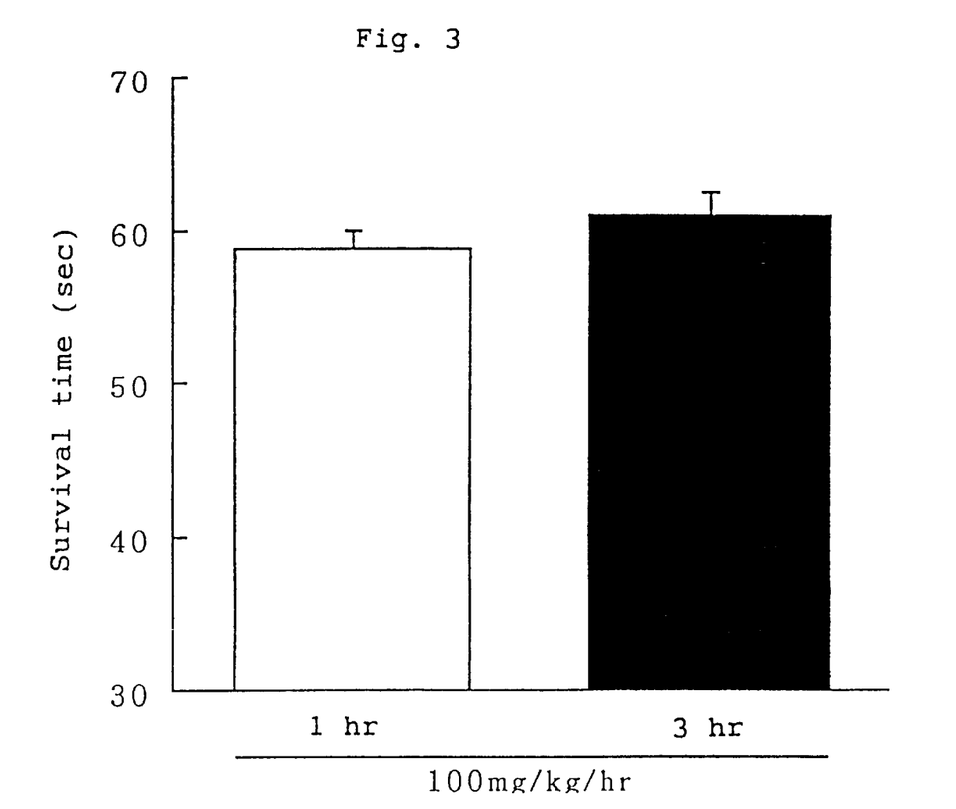
FIG. 3 shows the relationship between the duration of sodium β-hydroxybutyrate administration and the survival time.

FIG. 2 shows the relationship between the dose of sodium β-hydroxybutyrate and the survival time, while FIG. 3 shows the relationship between the duration of administration and the survival time.

The survival time was significantly prolonged by treatment with sodium β-hydroxybutyrate at 50 or 100 mg/kg/hr for 1 hour as compared with the physiological saline-receiving group (58.8±2.4 and 58.8±1.2 sec vs. 44.6±1.6 sec; FIG. 2). Although rats treated with Grenol also survived for longer than the physiological saline-receiving group, the difference was not statistically significant (52.8±2.3 sec vs. 44.6±1.6 sec; FIG. 2).

The survival time of rats treated withسodium β-hydroxybutyrate at 100 mg/kg/hr for 3 hours did not differ significantly from that of rats treated for 1 hour (61.0±1.6 sec vs. 58.2±2.2 sec; FIG. 3).

Potassium cyanide is believed to express its cytotoxicity by suppressing oxygen supply to the electron transport system and blocking ATP production through the inhibition of mitochondrial cytochrome oxidase. It has been reported that anti-anoxia mechanisms may include the promotion of cerebral glucose uptake, activation of the mitochondrial succinate oxidase system, and promotion of an increase in cerebral blood flow. β-hydroxybutyric acid, at the doses tested in this study, significantly suppressed the increase in cerebral water content induced by the bilateral common carotid arteries ligation (BLCL) for 6 hours. At the same dose levels, the compound significantly prolonged the survival time after potassium cyanide administration. In contrast, the Grenol-treated group did not show a significant increase in survival time as compared with the physiological saline-treated group. Based on these findings, the isotonic solution of β-hydroxybutyric acid may have suppressed the increase in the cerebral water content in the BLCL-induced cerebral edema model by activating cerebral metabolism, a mechanism different from the anti-edema effect of Grenol.

C): Cerebral metabolic activation:

Example 5

(Materials and methods)

1. Test animals

Male Wistar rats purchased from Japan S.L.C., Ltd. were used after a 1-week acclimatization period. The animals were maintained at 23±2° C. and 55±10% humidity with lights on for 12 hours daily (from 7:00 to 19:00). They were fed a pellet diet (MF, Oriental Yeast Co., Ltd.) and tap water ad libitum. Their weight averaged 172.1±6.7 g at the time of the study.

2. Test and control drugs

1) Test drug

Sodium β-hydroxybutyrate (BHBNa).

BHBNa remained stable for 5 months when stored at room temperature. Samples of the lot used in the study showed no changes in quality when tested after completion of the study. The solution was confirmed to remain stable for at least 1 week after preparation and to be prepared at a proper concentration.

2) Control drug

Physiological saline JP

Manufacturer: Otsuka Pharmaceutical Co., Ltd.

3. Experimental design

The dose of BHBNa tested was 25 mg/kg/hr. The test group was treated with a 20 mM BHBNa solution, while the control group received physiological saline. In both groups, administration was performed at a rate of 10 ml/kg/hr for 5 hours.

4. Test procedures

Rats were operated on under anesthesia which was introduced with ether and maintained by inhalation of a mixture of isoflurane/nitrous oxide/oxygen (0.5:70:30). A midline incision was made in the neck. The connective tissue was dissected carefully to avoid injury to the vagus nerves while exposing the bilateral common carotid arteries. The right external jugular vein was cannulated and the other end of the cannula was led out through the back. Each of the exposed common carotid arteries was ligated at two points (head side and heart side) and severed between the two ligatures. The skin incision was sutured and each rat was immediately given the test drug or physiological saline by continuous intravenous infusion using an infusion pump at a rate of 10 ml/kg/hr for 5 hours. In sham-operated rats, the bilateral common carotid arteries were exposed in the same way and the skin incision was closed without arterial ligation and severing. After completion of administration, each animal was sacrificed by decapitation and the whole brain was immediately isolated. After removal of the cerebellum and the medulla oblongata, the wet weight of the cerebrum was measured. The cerebrum was then dried at 105° C. for 24 hours and the dry weight was measured. The cerebral water content was calculated by using the following formula:

Cerebral water content (%)=(wet weight of the cerebrum−dry weight of the cerebrum)/wet weight of the cerebrum×100.

After weighing, the dried cerebrum was dissolved in 0.6 N $HNO_3$ (1 ml/100 g cerebrum) and subjected to wet combustion at 125° C. until a clear colorless product was obtained. To the combustion product, purified water was added to make up exactly 1 ml, and the solution was assayed for $Na^+$ and $K^+$ by using a flame photometer (FLAME-30C: Nihonbunko Medical Co., Ltd.). Groups of 9 rats were used in the study.

5. Statistical analysis

Data are expressed as the mean±standard error (S.E.). Differences between the groups were tested for significance by using one-way ANOVA, followed by Dunnett's multiple comparison test. The level of significance was set at $p<0.05$.

(Results)

Figure 4:
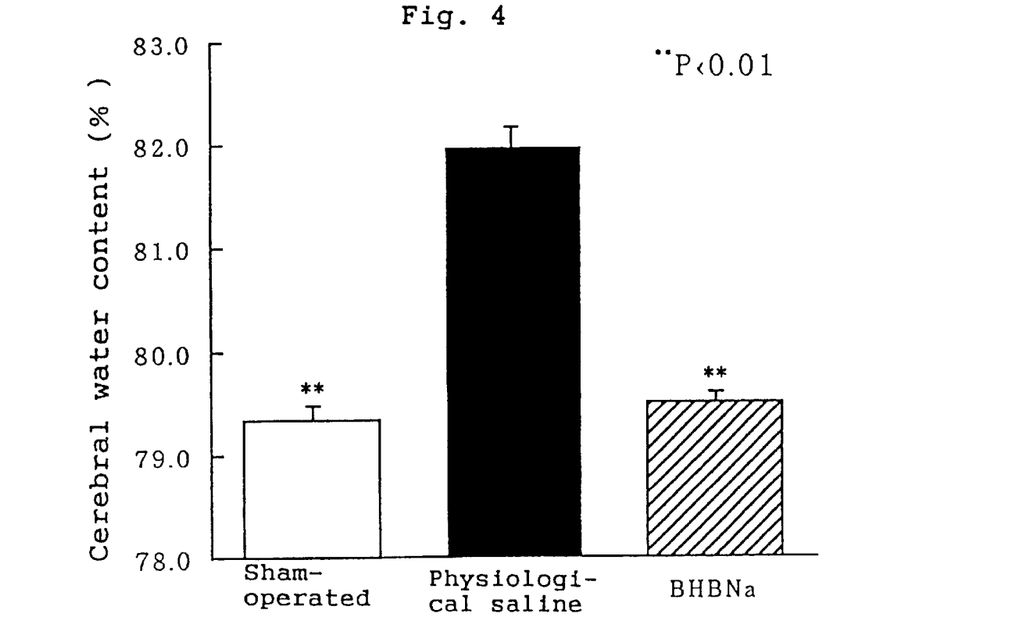
FIG. 4 shows the effect of sodium β-hydroxybutyrate on the cerebral water content.
Figure 5:
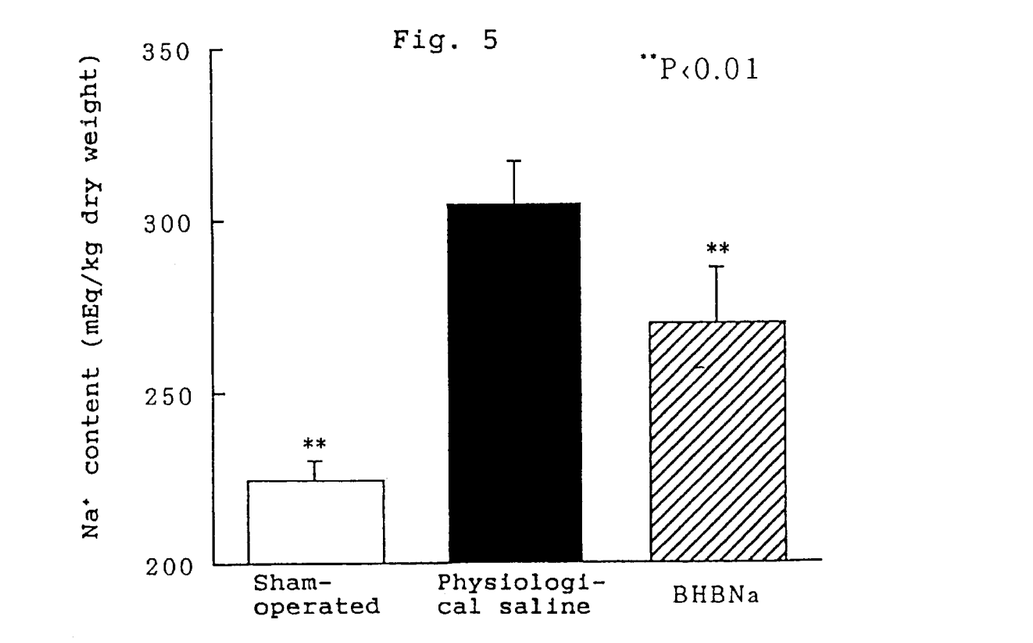
FIG. 5 shows the effect of sodium β-hydroxybutyrate on the cerebral $Na^+$ content.
Figure 6:
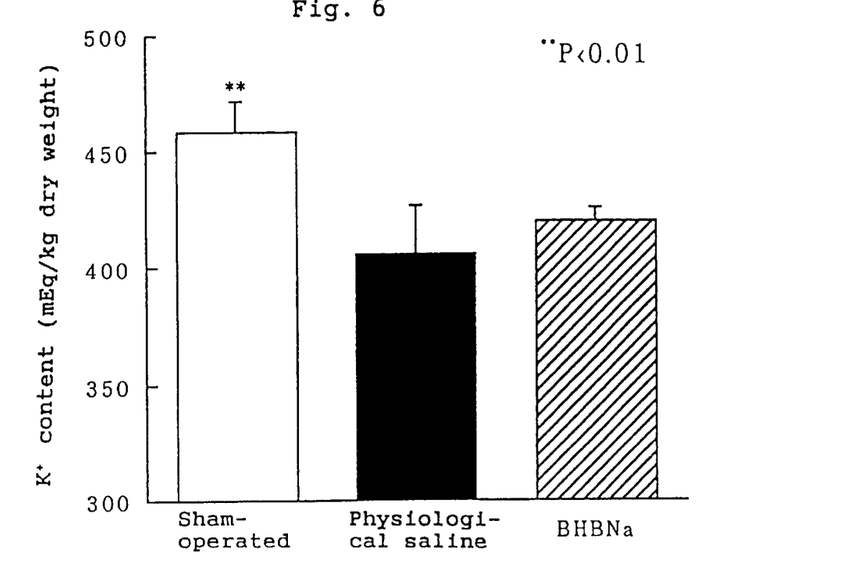
FIG. 6 shows the effect of sodium β-hydroxybutyrate on the cerebral $K^+$ content.

Data on the cerebral water and electrolyte content in rats with bilateral common carotid artery ligation with or without BHBNa treatment are shown in Table 1 and FIGS. 4–6.

TABLE 1

Cerebral water and electrolyte content

| Group (n = 9) | Cerebral water content (%) | Na+ content (mEq/kg dry weight) | K+ content (mEq/kg dry weight) |
|---|---|---|---|
| Sham-operated | 79.32 ± 0.16** | 224.08 ± 5.93** | 458.31 ± 13.44** |
| Physiological saline | 81.96 ± 0.21 | 304.39 ± 12.83 | 405.99 ± 20.96 |
| BHBNa | 79.50 ± 0.09** | 269.74 ± 15.98** | 420.42 ± 5.76 |

**P < 0.01 vs. Physiological saline group

The bilateral common carotid arteries ligation (BLCL) caused a significant increase in the cerebral water and Na+ content (p<0.01) as well as a significant decrease in the cerebral K+ content (p<0.01) in the physiological saline group compared with the sham-operated group. The rats receiving continuous infusion of BHBNa showed a significantly smaller increase in the cerebral water and Na+ content (p<0.01) as compared with the physiological saline-treated rats, although the cerebral K+ content did not differ significantly.

Example 6

(Materials and methods)
1. Test animals

Male Wistar rats (Japan S.L.C., Ltd.) were used in the study. The animals were maintained at 23±3° C. and 55±15% humidity with lights on for 12 hours daily (from 7:00 to 19:00). They were fed a pellet diet (MF, Oriental Yeast Co., Ltd.) and tap water ad libitum. Their weight ranged from 161.7 to 249.0 g at the time of the study.

2. Test and control drugs
  1) Test drug
    Sodium β-hydroxybutyrate (BHBNa).
  2) Control drug
    Glyceol (brand name)
      Composition (content per 100 ml)
      Concentrated glycerin 10 g
      Fructose 5 g
      Sodium chloride 0.9 g
    Distributor Chugai Pharmaceutical Co., Ltd.
  3) Vehicles
    (1) Vehicle 1
      Physiological saline JP
      Distributor: Otsuka Pharmaceutical Co., Ltd.
    (2) Vehicle 2
      Distilled Water for Injection JP
      Distributor: Otsuka Pharmaceutical Co., Ltd.

3. Preparation of the dosing solution

Exactly 0.2 g of BHBNa was weighed and dissolved in distilled water for injection to make a final volume of 10 ml. To 9 ml of this solution, physiological saline was added to make up 30 ml. The 0.6% BHBNa solution thus obtained was sterilized by filtration through DISMIC-25CS (0.2 μM, ADVANTEC Toyo) prior to use.

4. Preparation of a cerebral ischemia model

Rats were operated on under anesthesia which was introduced with ether and maintained by inhalation of a mixture of isoflurane/nitrous oxide/oxygen (0.5:70:30). A midline incision was made in the neck and the connective tissue was carefully dissected to avoid injury to the vagus nerve while exposing the bilateral common carotid arteries.

For test drug administration, the right external jugular vein was cannulated and the other end of the cannula was led out through the back of the animal. Then the common carotid artery was ligated at two points (head side and heart side) and severed between the two ligatures. The skin incision was closed and each rat was immediately given physiological saline, 0.6% BHBNa solution, or Glyceol by continuous intravenous infusion using an infusion pump at a rate of 5 ml/kg/hr. In sham-operated rats, the bilateral common carotid arteries were exposed and the skin incision was then dosed without arterial ligation and severing.

After 3 hours of cerebral ischemia, the head of each rat was irradiated with microwaves (5 kW) for 2 seconds using a microwave applicator (TMW6402C, Toshiba) to terminate all enzyme reactions and the production/degradation of metabolites in the brain tissue. The cerebrum was separated from the cerebellum and medulla oblongata and was placed in a pre-weighed test tube containing 3 ml of ice-cold 10% trichloroacetic acid (TCA). Then the test tube was weighed again. Next, the cerebrum was homogenized in TCA in an ice-cold bath using a homogenizer (Physcotron, Nichion). The homogenate was centrifuged at 3,000 rpm for 15 minutes at 4° C., and the supernatant was collected. The pellet was homogenized again in 2 ml of 10% TCA and the homogenate was centrifuged under the same conditions. The supernatant thus obtained was mixed thoroughly with the previous supernatant by stirring to use the mixture as the sample solution. The sample solution was divided into two equal portions, and to one portion, 3 ml of water-saturated ether was added. The mixture was stirred and centrifuged at 3,000 rpm for 15 minutes at 4° C., and the ether layer (supernatant) was removed. This extraction procedure was done three times, and the water phase thus obtained was assayed to determine the ATP content. The other portion of the sample solution was used to determine the lactate content. The weight of the cerebrum was calculated from the difference of the weight of the test tube measured as above.

The cerebral ATP level was determined by an enzymatic method (the luciferin-luciferase method) by using Lumat LB9507 (EG&G BERTHOLD). The data obtained were expressed as μmoles/wet weight g.

The cerebral lactate level was determined by an enzymatic method (lactate dehydrogenase method) by using Determiner LA (Kyowa Medics). The data obtained were expressed as μmoles/wet weight g.

5. Statistical analyses

Data are expressed as the mean±standard error (S.E.). Differences between the groups were tested for significance by using one-way ANOVA. When a significant difference was detected, Scheffe's multiple comparison test was performed. The level of significance was set at p<0.05.

(Results)

Figure 7:
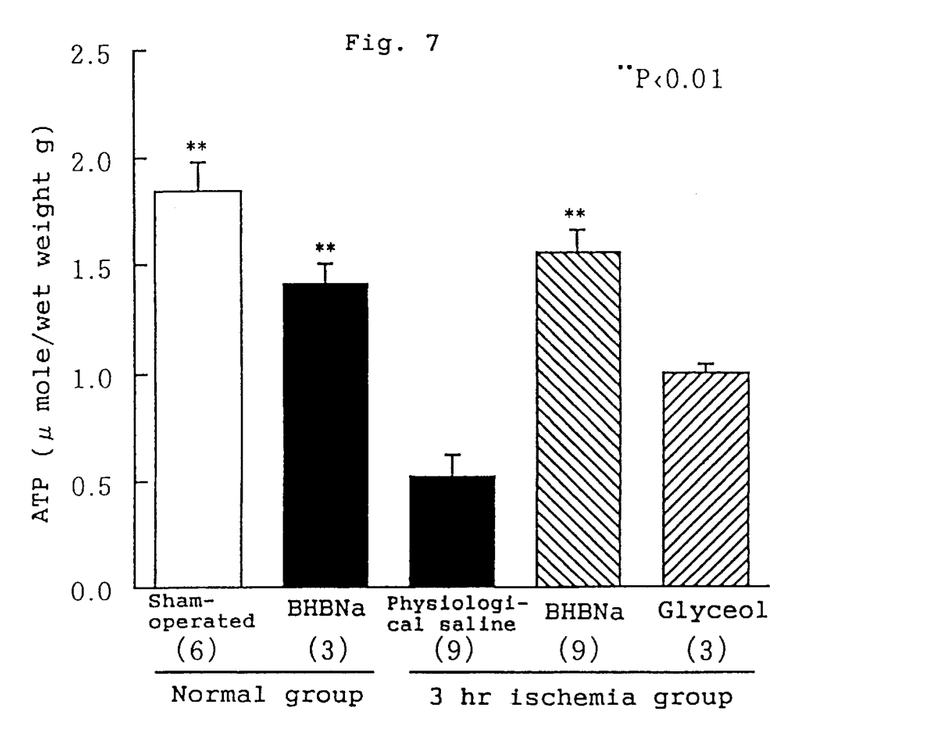
FIG. 7 shows the effect of sodium β-hydroxybutyrate on the cerebral ATP content.
Figure 8:
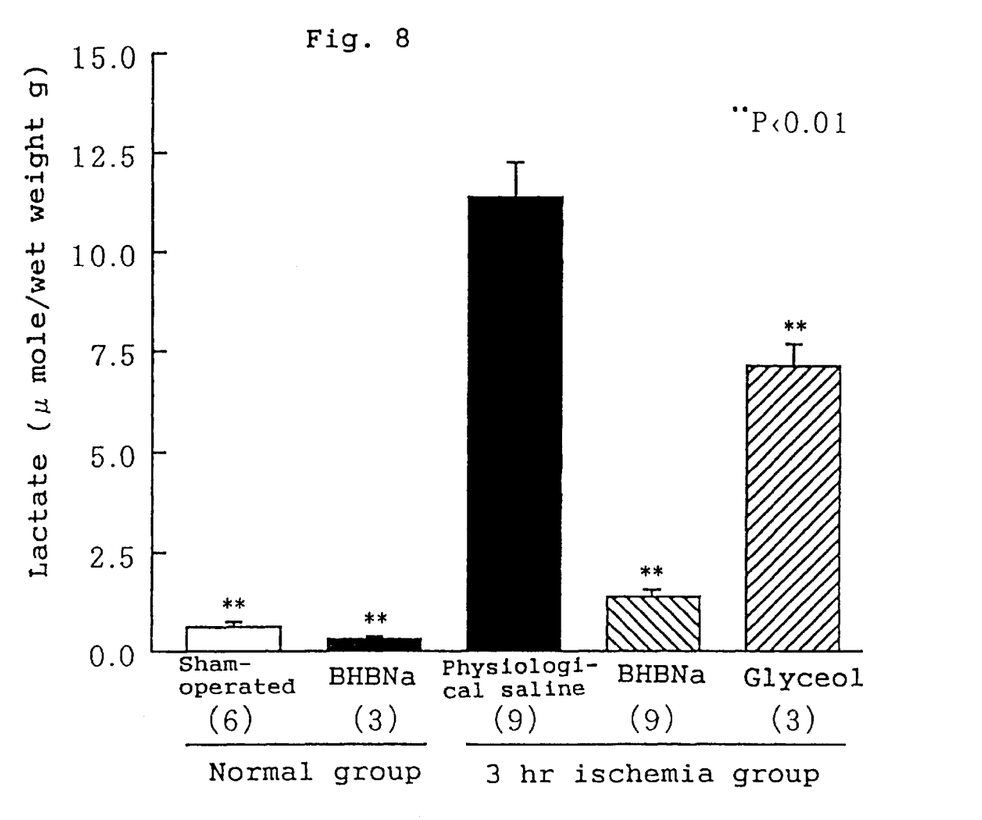
FIG. 8 shows the effect of sodium β-hydroxybutyrate on the cerebral lactate content.

Data on the cerebral ATP and lactate levels are shown in FIGS. 7 and 8, respectively.

1. Effect of BHBNa on the cerebral ATP and lactate levels in normal rats

Continuous infusion of BHBNa for 3 hours had no significant effect on the cerebral ATP or lactate level in normal rats without BLCL.

2. Effect of BHBNa and Glyceol on the cerebral ATP and lactate levels in rats with BLCL
  1) Cerebral ATP level The cerebral ATP level was significantly reduced after 3 hours of BLCL in the physiological saline-treated rats compared with the sham-operated rats (0.52±0.10 vs. 1.85±0.13 μmoles/wet weight g). The rats which received BHBNa at a dose of 30 mg/kg/hr during BLCL showed a significantly smaller decrease in the cerebral ATP level as compared with the physiological saline group, with the final value (1.56±0.10 μmoles/wet weight g) being similar to that in the sham-operated rats. Continuous infusion of Glyceol during BLCL produced no significant difference in the cerebral ATP level as compared with that in the physiological saline group (1.00±0.04 vs. 0.52±0.10 μmoles/wet weight g).

2) Cerebral lactate level

The cerebral lactate level was significantly increased after 3 hours of BLCL in the physiological saline-treated rats compared with the sham-operated rats (11.39±0.85 vs. 0.61±0.12 μmoles/wet weight g). Rats which received BHBNa at a dose of 30 mg/kg/hr during BLCL showed a significantly smaller increase in cerebral lactate as compared with the physiological saline group, with the final value being 1.36±0.17 μmoles/wet weight g. Rats receiving Glyceol during BLCL also showed a significantly smaller increase in cerebral lactate as compared with the physiological saline group (7.16±0.54 vs. 11.39±0.85 μmoles/wet weight g), but the final value was still significantly higher than in the sham-operated group.

D): Cerebral infarction reducing effect

Example 7

(Materials and methods)
1. Test animals

Male Wistar rats aged 8 weeks (Charles River Japan, Inc.) were used in the study. The animals were maintained at 23±3° C. and 55±15% humidity with lights on for 12 hours daily (from 7:00 to 19:00). They were fed a pellet diet (MF, Oriental Yeast Co., Ltd.) and tap water ad libitum. Their weight ranged from 270.6 to 338.9 g at the time of the study.

2. Test and control drugs
   1) Test drug
      Sodium β-hydroxybutyrate (BHBNa)
   2) Vehicles
      (1) Vehicle 1
         Physiological saline JP
         Distributor: Otsuka Pharmaceutical Co., Ltd.
      (2) Vehicle 2
         Distilled Water for Injection JP
         Distributor: Otsuka Pharmaceutical Co., Ltd.

3. Preparation of the test solution

The solution of BHBNa was prepared immediately before use.

Exactly 0.2 g of BHBNa was weighed and dissolved in distilled water for injection to make up a final volume of 10 ml. To 9 ml of this solution, physiological saline was added to make up 30 ml. The 0.6% BHBNa solution obtained in this way (a dose level of 30 mg/kg) was sterilized by filtration through DISMIC-25CS (0.2 μM, ADVANTEC Toyo) prior to use.

4. Preparation of a middle cerebral artery occlusion/reperfusion model
   1) Middle cerebral artery occlusion model Under ether anesthesia, a midline incision was made in the neck. The incision reached the right carotid bifurcation while avoiding injury to the vagus nerve. Around the bifurcation, the common carotid artery and the external carotid artery were separated from surrounding connective tissue and adipose tissue. The occipital and superior thyroid arteries arising from the external carotid artery were dissected out, double ligated with 6-0 silk, and cut. The external carotid artery was then double ligated with 5-0 silk and cut In addition, the right internal carotid artery was dissected out from the surrounding connective tissue to expose the pterygopalatine artery. The external carotid artery was incised, and an embolizing thread was inserted via this incision to a distance of 21 mm into the internal carotid artery. The tip of the thread went beyond the origin of the middle cerebral artery and entered the anterior cerebral artery by about 1–2 mm, so that the middle cerebral artery was occluded by the central portion of the thread.

In sham-operated rats, the skin incision was closed without inserting any embolizing thread into the internal carotid artery. The rats were then maintained until the scheduled time of sacrifice.

2) Reperfusion model

After the middle cerebral artery was occluded with an embolizing thread for 2 hours, the thread was removed under ether anesthesia to allow reperfusion.

5. Administration of the test and control drugs

Immediately after insertion of the embolizing thread, the rats were given a continuous infusion of physiological saline or 0.6% BHBNa solution via a cannula inserted into a femoral vein on the previous day. Administration was performed at a rate of 5 ml/kg/hr using an infusion pump and was continued until the scheduled time of sacrifice (24 hours after reperfusion).

6. Preparation of cerebral specimens

Each rat was sacrificed at 24 hours after reperfusion. The cerebrum was isolated, and cut into 2 mm coronal sections by using a Brain Slicer (MUROMACHI KIKAI Co., Ltd.) from a point 7 mm behind the edge of the forebrain to the interauricular line (telencephalon). The brain sections were stained to detect normal mitochondria by total immersion for 30 min in a 2% solution of 2,3,5-triphenyltetrazolium chloride (TTC) in physiological saline. The stained sections were fixed with 10% neutral buffered formalin.

7. Evaluation of brain sections

Photographs of the TTC-stained coronal sections of the cerebrum were scanned by using an film scanner and the data were processed with image analyzing software (NIH Image). The percent infarcted area (mitochondria death) on each cerebral section was calculated from the total area of the unstained regions relative to the entire area of the section.

(Results)

The percent infarction data obtained are shown in Table 2.

TABLE 2

| | Infarction data | |
|---|---|---|
| | | n = 4 |
| | Infarction % | S.E. |
| BHBNa | 18.99 | ±1.59 |
| Physiological saline | 35.18 | ±2.69 |

The mean percent infarction was 35.18±2.69% in the rats receiving a continuous infusion of physiological saline throughout the 2 hour period of middle cerebral artery occlusion and the subsequent 24 hour reperfusion period. Infarcts were found in the middle cerebral artery territory (temporal lobe), the anterior cerebral artery territory (parietal lobe), and the region in and around the striatum in the right cerebral hemisphere. These findings suggested that infarction may develop not only in the central ischemic region but also in the surrounding regions (parietal lobe and striatum) after occlusion of the middle cerebral artery.

On the other hand, continuous infusion of BHBNa (30 mg/kg/hr) immediately after arterial occlusion reduced the mean percent infarction to 18.99 ±1.59%. Most infarct foci were localized in the central ischemic zone and few extended to the surrounding regions.

Example 8
Toxicity Study
(1) BHBNa was orally or intravenously administered to Wistar or SD rats of both sexes at a single dose of 2000 mg/kg. The rats survived without any abnormal findings.
(2) BHBNa was repeatedly administered orally or intravenously to male Wistar or SD rats for 2 weeks. The rats given 500 mg/kg–2000 mg/kg survived without any abnormal findings.

Example 9
Formulation
The following components in the specified amounts were used to prepare parenteral solutions according to the appropriate procedures:

β-hydroxybutyric acid monoglycerate 16.0 g
Sodium chloride 3.15 g
Potassium chloride 0.30 g Each component was dissolved in about 950 ml of water, and the pH was adjusted to 7.0 with hydrochloric acid or sodium hydroxide. Then more water was added to make exactly 1,000 ml. The solution thus prepared was filtrated through a 0.20 μm membrane filter, and the filtrate was filled in a 500 ml glass container and autoclaved to give a precipitate-free, colorless parenteral solution.

Example 10
Other formulations
By using the components in the specified amounts listed in Table 3, precipitate-free, colorless parenteral solutions were obtained according to the procedures described above.

The abbreviations used in Table 3 are as follows:
BHB=β-hydroxybutyric acid;
BHBNa sodium β-hydroxybutyrate;
BHBMe=methyl β-hydroxybutyrate; and
BHB-oligo (3 mar)=oligomer (trimer) of β-hydroxybutyric acid.

infarction. These agents are therefore expected to be highly effective for the improvement of cerebral function.

What is claimed is:

1. A method for activating cerebral metabolism in a subject suffering from impaired cerebral metabolism comprising enterally or parenterally administering to the subject a composition comprising as an active ingredient a compound represented by the formula (1)

$$CH_3-\underset{\underset{R_2}{|}}{\overset{\overset{R_1}{|}}{C}}-CH_2-COO-R_3 \tag{1}$$

wherein $R_2$ represents a hydrogen atom when $R_1$ is a hydroxyl group; or $R_1$ and $R_2$ are combined together to form an oxo group;

$R_3$ represents a hydrogen atom, an alkali metal or a monohydric, dihydric or trihydric alcohol residue, which may be an oligomer composed of 2–10 molecules when $R_1$ represents a hydroxyl group and $R_2$ and $R_3$ represent hydrogen atoms.

2. A method for retaining cerebral ATP content comprising enterally administering to a subject suffering from cerebral edema or cerebral infarction a composition comprising as an active ingredient a compound represented by the formula (1)

$$CH_3-\underset{\underset{R_2}{|}}{\overset{\overset{R_1}{|}}{C}}-CH_2-COO-R_3 \tag{1}$$

wherein $R_2$ represents a hydrogen atom when $R_1$ is a hydroxyl group; or $R_1$ and $R_2$ are combined together to form an oxo group;

$R_3$ represents a hydrogen atom, an alkali metal or a monohydric, dihydric or trihydric alcohol residue,

TABLE 3

List of components and the amounts

| | BHB | BHBNa | BHBMe | BHB-oligo (3mar) | NaCl | KCl | (g/l) Glucose |
|---|---|---|---|---|---|---|---|
| (1) | 31.2 | — | — | — | 2.05 | 1.47 | 50 |
| (2) | 2.42 | — | — | — | 2.05 | 1.47 | 50 |
| (3) | 15.6 | — | — | — | 7.02 | 1.47 | 50 |
| (4) | 2.42 | — | — | — | 7.02 | 1.47 | 50 |
| (5) | — | 16.4 | — | — | 0.585 | — | 50 |
| (6) | — | 16.4 | — | — | — | 1.47 | 50 |
| (7) | — | — | 36.3 | — | 2.05 | 1.47 | 50 |
| (8) | — | — | 18.15 | — | 7.02 | — | 50 |
| (9) | — | — | 2.42 | — | 7.02 | 1.47 | 50 |
| (10) | — | — | — | 46.5 | 2.05 | 1.47 | 50 |
| (11) | — | — | — | 6.2 | 2.05 | 1.47 | 50 |
| (12) | — | — | — | 46.5 | 7.02 | 1.47 | 50 |
| (13) | — | — | — | 6.2 | 7.02 | 1.47 | 50 |

As described above, the cerebral function improving agents of the present invention; which contain the compounds of formula (1) as the active ingredient, can suppress cerebral edema, protect cerebral function, improve impaired cerebral metabolism, and reduce the extent of cerebral which may be an oligomer composed of 2–10 molecules when $R_1$ represents a hydroxyl group and $R_2$ and $R_3$ represent hydrogen atoms.

3. A method for suppressing cerebral edema comprising enterally administering to a subject suffering from cerebral edema a composition comprising as an active ingredient a compound represented by the formula (1)

(1)

wherein $R_2$ represents a hydrogen atom when $R_1$ is a hydroxyl group; or $R_1$ and $R_2$ are combined together to form an oxo group;

$R_3$ represents a hydrogen atom, an alkali metal or a monohydric, dihydric or trihydric alcohol residue, which may be an oligomer composed of 2–10 molecules when $R_1$ represents a hydroxyl group and $R_2$ and $R_3$ represent hydrogen atoms.

4. A method for reducing cerebral infarction comprising enterally administering to a subject suffering from cerebral infarction a composition comprising as an active ingredient a compound represented by the formula (1)

(1)

wherein $R_2$ represents a hydrogen atom when $R_1$ is a hydroxyl group; or $R_1$ and $R_2$ are combined together to form an oxo group;

$R_3$ represents a hydrogen atom, an alkali metal or a monohydric, dihydric or trihydric alcohol residue, which may be an oligomer composed of 2–10 molecules when $R_1$ represents a hydroxyl group and $R_2$ and $R_3$ represent hydrogen atoms.

5. A method as claimed in claim 1 wherein the composition comprises as an active ingredient from 5 to 500 mM of the compound of formula (1).

6. A method as claimed in claim 2, wherein the composition comprises as an active ingredient from 5 to 500 mM of the compound of formula (1).

7. A method as claimed in claim 3, wherein the composition comprises as an active ingredient from 5 to 500 mM of the compound of formula (1).

8. A method as claimed in claim 4, wherein the composition comprises as an active ingredient from 5 to 500 mM of the compound of formula (1).

* * * * *

UNITED STATES PATENT AND TRADEMARK OFFICE
CERTIFICATE OF CORRECTION

PATENT NO. : 6,232,345 B1
DATED : May 15, 2001
INVENTOR(S) : Atsushi Hiraide et al.

It is certified that error appears in the above-identified patent and that said Letters Patent is hereby corrected as shown below:

<u>Title page,</u>
Item [63], replace "Continuation of application No. 08/756,747, filed on Jan. 26, 1996, now Pat. No. 6,136,862". with -- Continuation of application No. 08/756,747, filed on Nov. 26, 1996, now Pat. No. 6,136,862. --

Signed and Sealed this

Second Day of April, 2002

Attest:

Attesting Officer

JAMES E. ROGAN
*Director of the United States Patent and Trademark Office*